United States Patent [19]

Ohara et al.

[11] 4,360,324
[45] Nov. 23, 1982

[54] PULSATILE BLOOD PUMP

[75] Inventors: Shozo Ohara; Toshio Ichinose, both of Tokyo, Japan

[73] Assignee: Nikkiso, Co. Ltd., Japan

[21] Appl. No.: 123,960

[22] Filed: Feb. 25, 1980

Related U.S. Application Data

[63] Continuation-in-part of Ser. No. 773,602, Mar. 2, 1977, abandoned.

[30] Foreign Application Priority Data

Nov. 9, 1976 [JP] Japan .................. 51-133785

[51] Int. Cl.³ ............................................ F04B 35/02
[52] U.S. Cl. .................. 417/388; 417/394; 417/478
[58] Field of Search ............... 417/383, 385, 478, 394, 417/388, 479, 480; 74/40, 45, 53, 54, 55

[56] References Cited

U.S. PATENT DOCUMENTS

| 723,042 | 3/1903 | Schwerin | 417/478 |
|---|---|---|---|
| 1,319,213 | 10/1919 | Engelbrekt | 74/53 |
| 1,742,746 | 1/1930 | Zubaty | 74/53 |
| 1,806,268 | 5/1931 | Schulze | 74/53 |
| 1,976,415 | 10/1934 | Scott | 417/478 X |
| 1,979,195 | 10/1934 | Govare et al. | 74/55 |
| 2,267,280 | 12/1941 | Kuhnel | 417/480 X |
| 2,735,642 | 2/1956 | Norman | 251/5 |
| 3,070,089 | 12/1962 | Dick | 417/478 X |
| 3,095,750 | 7/1963 | Mahn | 74/55 |
| 3,127,845 | 4/1964 | Voelcker | 417/478 |
| 3,148,624 | 9/1964 | Baldwin | 417/478 X |
| 3,194,164 | 7/1965 | Fink et al. | 92/13.2 X |
| 3,218,979 | 11/1965 | Baldwin | 417/478 X |
| 3,250,226 | 5/1966 | Voelker | 417/478 X |
| 3,551,076 | 12/1970 | Wilson | 417/478 X |
| 3,811,800 | 5/1974 | Shill | 417/394 X |
| 3,883,272 | 5/1975 | Puckett | 417/478 X |

FOREIGN PATENT DOCUMENTS

| 673217 | 3/1939 | Fed. Rep. of Germany | 417/388 |
|---|---|---|---|
| 103439 | 1/1942 | Sweden | 92/13.2 |
| 305235 | 2/1929 | United Kingdom | 417/383 |

*Primary Examiner*—Robert E. Garrett
*Assistant Examiner*—Edward Look

[57] ABSTRACT

A pulsatile blood pump comprising a disposable power bladder of flexible and anticoagulative material which is provided with a suction port with an inlet check valve and a delivery port with an outlet check valve to constitute a blood pump unit and hermetically sealed container for receiving said blood pump unit, said container being connected to a pulsating mechanism and filled with a pressure transmissive fluid which is subjected to a pulsatile pressure generated by the pulsating mechanism to vary the volume of the power bladder for pulsatile blood delivery.

4 Claims, 20 Drawing Figures

Stroke Volume: Mean (15cc/Beat)
A Number of Pulsation : 60 BPM

FIG.11-B

Stroke Volume: Mean (15cc/Beat)
A Number of Pulsation : 85 BPM

FIG.11-C

Stroke Volume: Mean (15cc/Beat)
A Number of Pulsation : 120 BPM

Hemolytic Test in Clinical Example

FIG.11-H

Cam

PULSATILE BLOOD PUMP

RELATED APPLICATION

This is a continuation-in-part of Ser. No. 773,602 now abandoned filed Mar. 2, 1977.

BACKGROUND OF THE INVENTION

The present invention relates to an improved pulsatile blood pump and more particularly a blood circulating pump which is adapted for surgical heart treatments.

Recently, various extracorporeal heart devices with blood pump have been proposed to circulate the blood through an extracorporeal circuit in an open heart surgery such as a cardiac transplantation.

Hitherto, a blood pump of the type referred to has been arranged so that an elastic sleeve is engaged with a plurality of rollers which turn at a predetermined velocity for squeezing the sleeve to obtain a desired transfer of the blood.

The circulation of the blood should physiologically be pulsatory like the human heart pulsation and in this view a pump of ordinary type which operates at a constant flow rate should not be used to transfer the blood for the prolonged period as it undesirably affects the flow characteristics of the vascular system.

To overcome many difficulties and inconveniences in the conventional blood pumps, it has been proposed for instance to use a reciprocating pump as generally employed in mechanically oriented industry for obtaining a desired pulsatile blood flow or a tube pump in which the turning motion of the roller in engagement with the sleeve pump chamber is variably controlled to obtain a desired pulsatile blood flow.

However, in the reciprocating pump of the type referred to an intricate vascular flow is likely caused with undesired stagnation and oscillation of the blood resulting in developments of undesired blood-destruction (hemolysis) and coagulation. While, the tube pump needs an intricate and uneconomical control means for producing a desired pulsatile blood flow approximate to the physiological pulsation.

Moreover, the blood pump once used must be cleansed and sterilized perfectly. However, the conventional pumps are unsuitable to satisfy such the important medical condition on account of the inconvenient cleansing treatment and the excessive consumption.

Further, prior art pumps are subject to a number of objection and disadvantages for such use. Some have a traumatic effect on the blood cells, some present a problem of sterilization, some produce excessive pulsations of the blood, some cannot be connected into the blood circuit and put into operation quickly and conveniently and some are objectionably complicated and expensive to manufacture.

According to the present invention, a novel pulsatile blood pump which comprises a disposable pump chamber and a pulsating mechanism producing a desired blood flow proximate to the physiological pulsation.

It is, therefore, a general object of the invention to provide a pump of the type described which is relatively simple in structure, inexpensive to manufacture, reliable and essentially trouble free in deterging or sterilizing treatment and enables to produce a pulsatile blood flow substantially proximate to the physiological pulsation.

SUMMARY OF THE INVENTION

In accordance with the invention, a power bladder of flexible and anticoagulative material is formed into a substantially U shape and provided with a suction port having an inlet check valve and a delivery port having an outlet check valve to constitute a pump unit which is placed in a hermetically sealed container which is filled with a pressure transmissive fluid such as biological saline solution harmless to the human body and subjected to a pulsatile pressure generated by the pulsating mechanism as hereinafter fully described.

Thus, a principal object of the invention is to provide a pulsatile blood pump comprising a disposable power bladder of flexible and anticoagulative material which is provided with a suction port having an inlet check valve and a delivery port having an outlet check valve to constitute a blood pump unit and a hermetically sealed container for receiving said blood pump unit, said container being connected to a pulsating mechanism and filled with a pressure transmissive fluid which is subjected to a pulsatile pressure generated by the pulsating mechanism to vary the volume of the power bladder for pulsatile blood delivery.

The suction and delivery ports of the power bladder are fixed in communication to openings provided in one side wall of the container.

In another embodiment of the invention, the disposable power bladder of anticoagulative material is formed into a substantially dome shape which at its curved portion is provided with a suction port having an inlet check valve and a delivery port having an outlet check valve whereas the straight portion of the power bladder is confronted with flexible diaphragm to provide a pressure transmission chamber therebetween and this chamber is connected to a pulsating mechanism and filled with a pressure transmissive fluid which is subjected to a pulsatile pressure generated by the pulsating mechanism to vary the volume of the power bladder for pulsatile blood delivery.

Another object of the invention is, therefore, to provide a pulsatile blood pump which comprises a disposable power bladder of flexible and anticoagulative material which at its one lateral portion is provided with a suction port with an inlet check valve and a delivery port with an outlet check valve to constitute a blood pump unit and a pressure transmission chamber arranged in abutment with the opposite lateral portion of the power bladder, said pressure transmission chamber being connected to a pulsating mechanism and filled with a pressure transmissive fluid which is subjected to a pulsatile pressure generated by the pulsating mechanism to vary the volume of the power bladder for pulsatile blood delivery.

In accordance with the present invention, the pulsating mechanism comprises for example a cam mechanism which produces a motion conformable to the physiological pulse and is connected through a stroke control means, a connecting rod and a piston to a diaphragm contacting with the power transmissive fluid.

Such cam mechanism however is not useful for the transfer at the blood of different pulse due to characteristics or physical conditions of the patient unless the cam is modified to conform with the different pulse of the patient.

To solve the foregoing inconvenience, in accordance with the present invention, a link mechanism is employed to convert a rotary motion into a reciprocal motion where a first link at its one end is connected to a rotary shaft for circulating and a second link at its one end is connected to a reciprocating member whereas an opposite end of the second link is pivoted to a connecting member slidably mounted on the first link and to the connecting member is pivoted a third link at its one end whereas an opposite end thereof is movable in the radial direction against an axis of the rotary shaft for adjustment so that an optimum blood pulsation may be obtained by bringing a movable end of the third link to the axis of the rotary shaft and leaving the movable free end of the third link from the axis of the rotary shaft along the radial direction.

Accordingly, it is a further object of the invention to provide a pulsatile blood pump which comprises a disposable blood pump unit, a container adapted to receive the blood pump unit and a pulsating mechanism connected to the container, said pulsating mechanism including a volume controlled reciprocating pump adapted to convert a rotary motion of a variable speed pump into a reciprocating motion through a crank mechanism and a stroke adjusting mechanism, said crank mechanism being capable of adjusting a reciprocating stroke of the pump and connected to a driving shaft turnable by means of a variable speed motor and including first, second and third links, said first link being connected to a rotary driving shaft for turning and ends of the second and third links being pivoted to a sliding member mounted on the first link for reciprocating the second link whereas an opposite end of the third link being connected to an adjusting shaft which shifts radially against an axis of the rotary driving shaft, said adjusting shaft being displaced for variable adjustment of the reciprocating stroke of the pump.

In a further embodiment of the invention, the pulsating mechanism comprises a stroke length adjustable reciprocating pump mechanism a driving shaft of which is connected through a releasable coupling to a driving shaft of a variable speed motor, so that the turning speed of the variable speed motor, the stroke length of the reciprocating pump and the releasing operation of the coupling may be conveniently controlled to obtain a desired blood pulsation synchronous with the physiological pulsation.

Still a further object of the invention is, therefore, to provide a pulsatile blood pump which comprises a disposable blood pump unit, a container adapted to receive the blood pump unit and a pulsating mechanism connected to the container, said pulsating mechanism comprising a driving motor with a speed control mechanism, a stroke length adjustable reciprocating pump mechanism and a releasable coupling means disposed between the driving motor and the reciprocating pump for engagement and disengagement to obtain a desired pulsatile blood flow synchronizing with the physiological pulsation.

In order to synchronize the blood flow with the physiological pulsation, it is preferred to provide a detecting means for measuring and converting a pulsation of the vascular or blood circuitry system of the human body into a pulse signal and a servo mechanism which receives the pulse signal from the detecting means to control the speed of the driving motor, the stroke length of the reciprocating pump mechanism and a degree of engagement as well as disengagement of the coupling.

In the reciprocating mechanism of the pump intended to be used in the present invention, a driving torque reduction means is arranged to reduce the maximum driving torque of the pump and this torque reduction means comprises an elastic member such as coil spring mounted in the reciprocating mechanism of the pump to conserve energy in the suction stroke of the pumping operation and release the energy in the delivery stroke.

The invention will be better understood and additional objects and advantages will become apparent from the following description of the preferred embodiment illustrated in the accompanying drawings. Various changes may be made, however, in the details of construction and arrangement of parts and certain features may be used without others. All such modifications within the scope of the apended claims are included in the invention. Although the invention is described in connection with pumping of blood, it is to be understood that the pump is of general application and may be used for other purposes.

BRIEF DESCRIPTION OF THE DRAWINGS

The invention will be described in greater detail with reference to the accompanying drawings, wherein:

FIG. 11, views A–J show the formation of a cam for generating wave patterns and their use.

DESCRIPTION OF THE INVENTION

Figure 1:
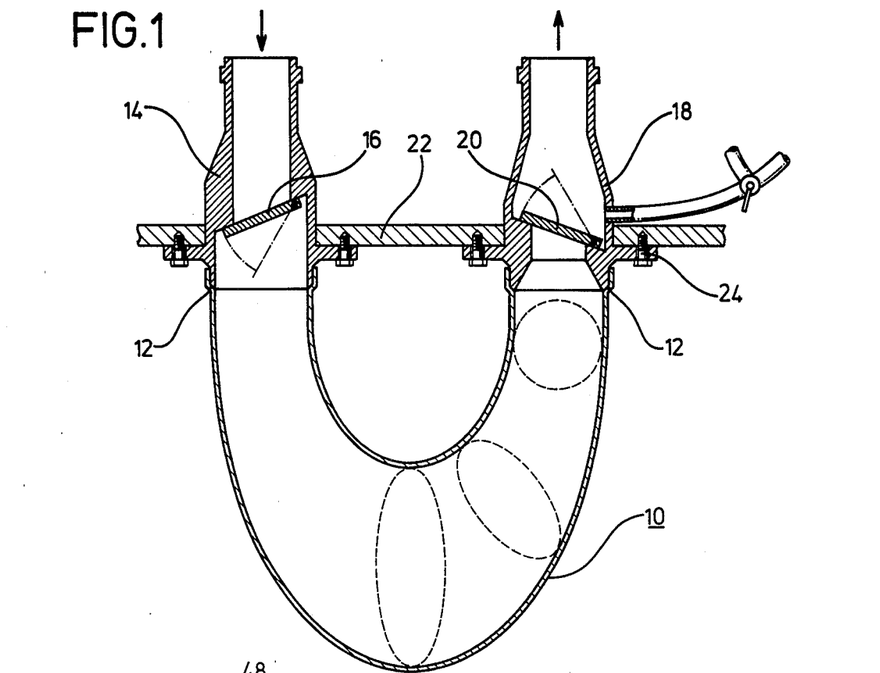
FIG. 1 is a front elevation of the blood pump unit in accordance with the present invention.
Figure 2:
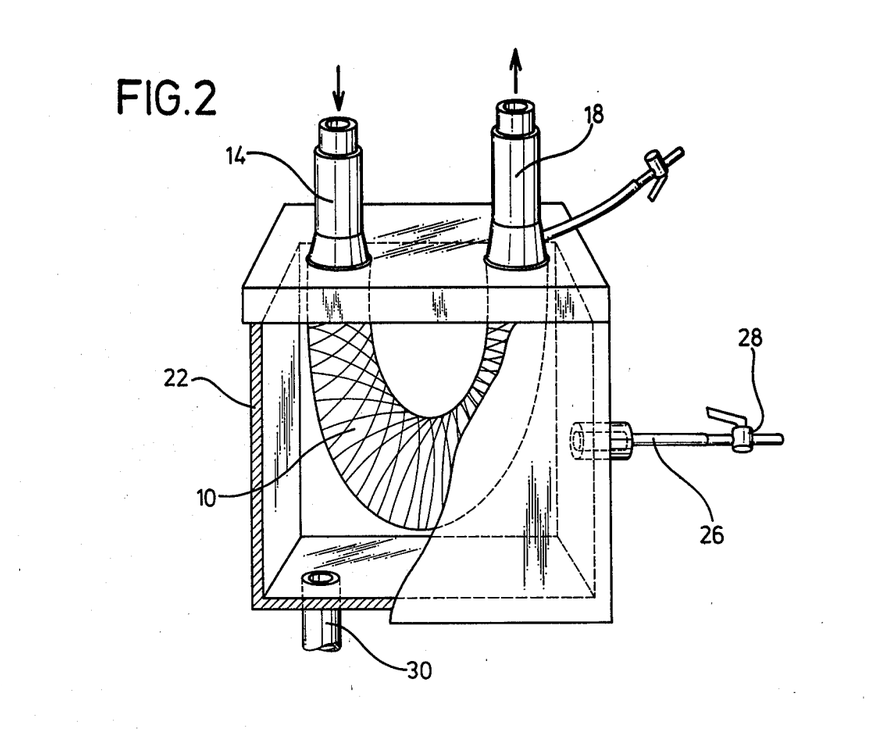
FIG. 2 is a partially sectioned perspective view of the pressure transmission chamber for accommodating the blood pump unit of FIG. 1.

In FIGS. 1 and 2, the reference numeral 10 is directed to a tubular power bladder of flexible and anticoagulative material formed into a substantially U shape, the opposite open ends of the bladder communicate respectively with a flanged suction port member 14 having an inlet check valve 16 and a flanged delivery port member 18 having an outlet check valve 20 to constitute a pump unit. The suction and delivery port members are also preferably formed of anticoagulative material.

The pump unit thus formed is recieved in a hermetically sealed container or chamber 22 and the suction and delivery port members 14 and 18 are secured to one side wall of the chamber 22 through convenient fasteners 24 as best shown in FIG. 1.

The chamber 22 is filled with a pressure transmissive fluid which is usually a saline solution harmless to the human body.

From the chamber 22 air is withdrawn by a degassing conduit 26 having a cock 28. A pipe 30 extends through its wall in communication with a pulsating mechanism as hereinafter fully described for imparting a desired pulsatile pressure to the fluid in the chamber with subsequent transmission to the power bladder for the pulsatile volume variation thereof.

The power bladder after a single use may be discarded for replacement by a fresh one without requiring any intricate treatment. Thus, it will be appreciated that the disposable blood pump in accordance with the invention may be obtained conveniently and at a reduced cost.

Figure 3:
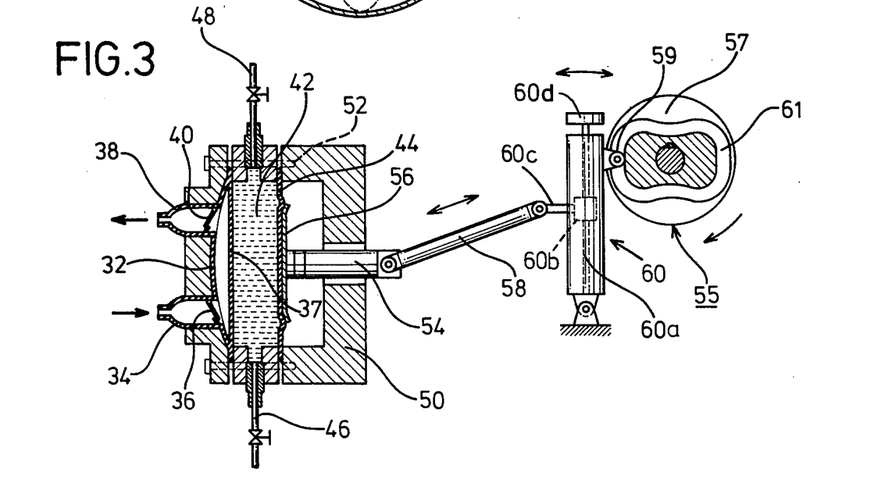
FIG. 3 is a longitudinally sectioned view of the pulsatile blood pump of another embodiment in accordance with the present invention.

In the embodiment as shown in FIG. 3, a domed shaped power bladder is formed by a curved portion 32 and a flat portion 37. The curved portion 32 is provided with a suction port 34 having an inlet check valve 36 and a delivery port 38 having an outlet check valve 40. In abutment with a straight portion 37 of the power bladder there is arranged a pressure transmission chamber 42 by locating a diaphragm 44 spared from the flat bottom portion 37. The chamber 42 receives the pressure transmissive fluid such as the saline solution. From the pressure transmission chamber 42 extend a fluid charging pipe 46 and a degassing pipe 48.

The power bladder formed by the curved portion 32 and the flat portion 37 and the pressure transmission chamber 42 are detachably secured to a support casing 50 by means of convenient fasteners 52—which seal the chamber 42.

The pressure transmission chamber 42 is compressed by a piston 54 through a support plate 56 which acts directly on the diaphragm 44. The piston 54 is connected to a cam mechanism 55 through a connecting rod 58 and a stroke adjusting mechanism 60. The cam mechanism 55 is designed so as to produce a rotary motion conforming to the physiological pulsation.

Namely, a cam disc 57 is provided with an eccentric channel 61 along which a follower 59 connected to a stroke adjusting mechanism 60 travels when the cam disc 57 is turned. The stroke adjusting mechanism, comprises a cylindrical sleeve which is pivotably mounted at its lower end. Extending axially through the sleeve is a screw 60a on which a thread boss 60b rides. The threaded boss is provided with a fixed arm 60c extending radially out of the sleeve to which the link 58 is pivotally attached. The cam follower 59 is pivotally attached at the upper end of the sleeve. By adjusting the position of the boss 60b along the length of the screw 60a, the fulcrum of the link 58 is varied and its stroke is thus adjustable. Adjustment of the boss 60b can be effected easily by manipulation of the pawl 60d on the upper end of the screw 60a, or by connection to a servo controlled device such as piston-cylinder operated ratchet, meshing in known manner with the pawl 60d.

Figure 4:
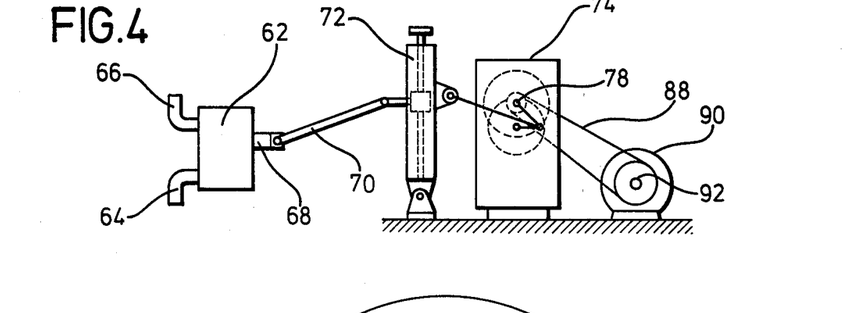
FIG. 4 is a side elevation view of another pulsating mechanism according to the invention.
Figure 5:
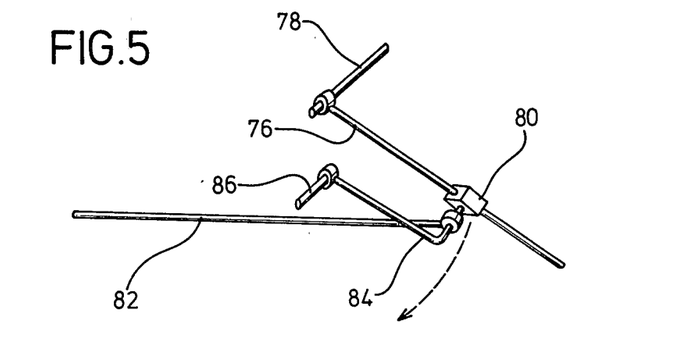
FIG. 5 is a fragmentarily enlarged perspective view of the link structure employed in the embodiment of FIG. 4.
Figure 6:
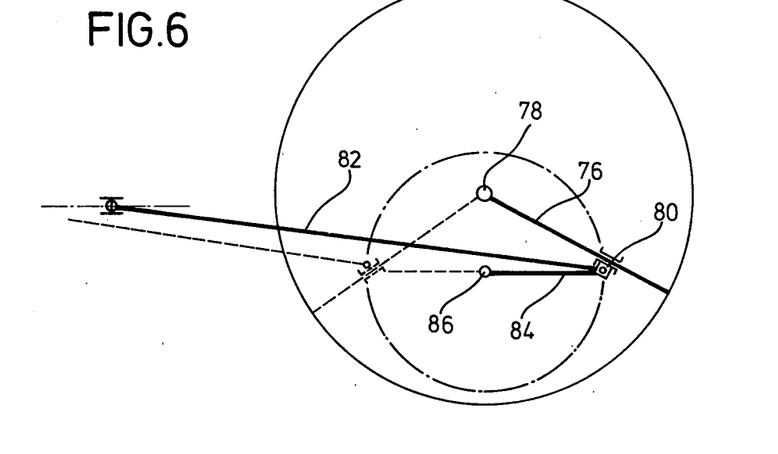
FIG. 6 is a pictorial view of the operational principles of the link structure of FIG. 4.

FIGS. 4 to 6 show another embodiment of the pulsating mechanism in which the reference numeral 62 stands for a pump having a suction port 64 and a delivery port 66, which is compressed by a reciprocating member 68 connected through a connecting rod 70 to a stroke length adjusting mechanism 72 which is in turn connected to a link mechanism 74 for converting the rotary motion into the reciprocal motion with continuous variable control of the reciprocating stroke.

As seen in FIG. 4, the link mechanism comprises a rotary driving shaft 78 which is driven by the driving shaft 92 of a variable speed motor 90 through a convenient power transmission member such as a pulley and belt system 88.

In FIGS. 5 and 6, the conversion of the rotary motion is seen to be accomplished by a first link 76, which at its one end is connected normally to the rotary driving shaft 78 for turning, and extend through a sliding member 80 which is movable along the axis of the link 76. To the sliding member 80 and offset therefrom is pivoted the end of a third link 84 and a second link 82 which serves as a crank for converting the turning motion of the first link 76 into the reciprocating motion. The opposite end of the second link 82 is connected to the connecting rod 70 of the stroke length adjustable mechanism 72. Further, an opposite end of the third link 84 is connected normally to an adjustable axis 86 which is radially movable relative to the rotary driving shaft 78. As seen in FIG. 6, the link 76 makes a circle (solid lines) about its center of the shaft 78, while link 84 makes a circle (dotted lines) about its axis 86. Due to the fact that the end of the link 84 is journalled in slidable member 80 both links 76 and 84 will rotate without interference. It has been confirmed that the pump operation at the systole as well as the diastole may be properly controlled by increasing or decreasing the distance between the adjusting shaft 86 and the rotary driving shaft 78.

Since the link 84 is pivotably secured at the end opposite 86 to the member 80 which member 80 is slidable on the link 76 in the axial direction, the link 84 as seen in FIG. 6 (and also in FIG. 4) describes a circular locus (dot-dash lines) about its center 86, while the link 76 describes a circular locus (solid lines) about its center 78. The two circles are clearly capable of being formed by the use of the slidable interconnection of member 80 which permits relative movement between the two.

Because the axle 86 is movable radially with respect to the axle 78, the position of the circular locus of link 84 (dot-dash lines) relative to the circular locus of link 76 (solid lines) is adjustable, thus creating the ability of moving the member 80 toward or away from the vertical lever 72 as seen in FIG. 4. The stroke length of the stroke adjusting mechanism is thus easily obtained.

Figure 7:
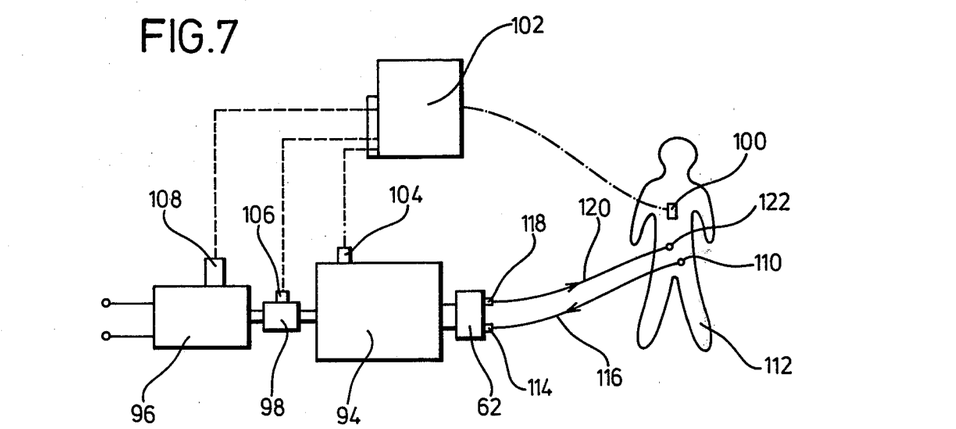
FIG. 7 is a pictorial view of a pulsating mechanism of another embodiment of the invention.
Figure 10:
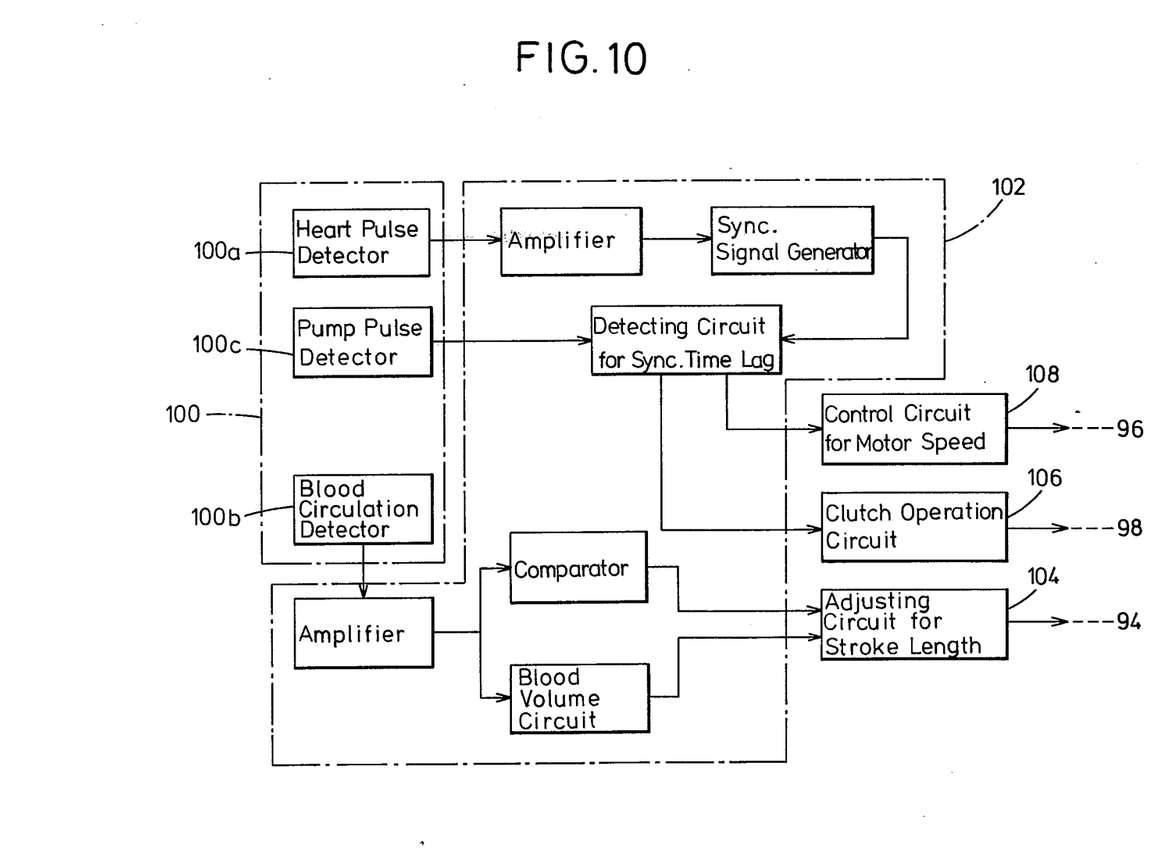
FIG. 10 is a schematic block diagram of the detection and control circuits for operating the device of the present invention.

In FIG. 7, a stroke length adjustable reciprocating pump mechanism 94 is arranged in abutment with the pump chamber 62 and connected through a releasable coupling 98 to a driving motor 96 having a variable speed mechanism (not shown). In this arrangement, as seen in FIG. 10, the turning rate of the driving motor 96, the stroke length of the reciprocating pump 94 and the degree of engagement and disengagement of the coupling 98 are conveniently compensated to obtain a desired pulsatile blood flow conforming to the physiological pulsation.

To control automatically the foregoing compensation in synchronism to the pulsation of the vital vascular system, a detector 100 is used to measure a signal (electrocardic or blood pressure) and a total controller 102 is adapted to receive the signal from the dector 100 for analysis of the pulsation rate, (heart pulse detector 100a), amount, (blood circulation detector 100b) and phase (pump pulse detector 100c) to generate the corresponding signals which are received by servo-mechanisms 104, 106 and 108 associated with the reciprocating pump mechanism 94, the coupling 98 and the driving motor 96 respectively for suitable controls of these units thereby to obtain the most desired blood pulsation.

The heart pulse signal is fed from the detector 100a via amplifier and a synchronous pulse generator to a companion circuit, which is also fed with the pulse signal from the pump pulse detector 100c. The comparison circuit determines the lag time between the actual heart pulse rate and the pump pulse rate and feeds a control pulse to the servo-mechanism 108 for the drive motor and to the servo-mechanism 106 for the pump. The blood circulation detector pulse signal is simultaneously fed to an amplifier, from which the amplified signal is fed to a comparator and volume control circuit which provides a control signal for the stroke adjustment servo-mechanism 104.

By the use of suitable comparison circuits, in the total controller, the actual pulse detected by the electrocardiac or blood pressure detector can be compared and synchronized with the pulse output of the pump chamber 62 and any difference between the two converted into an electrical signal can be used to operate the servo-mechanism 104, 106, 108 for regulating the respective pump, coupling and driving motor, to provide, the capacity of stroke, length of stroke and volume of blood desired.

In the open heart surgery of the human body, a preferred pump operation may be achieved by a simple manual operation of the servo-mechanisms 104, 106 and 108 without however actuating the automatic controller 102. The blood is withdrawn from an artery exit 110 of the human body 112 and directed to the suction port 114 of the pump 62 through a blood tube and subsequently the blood flow is fed back from the delivery port 118 through a blood tube 120 into a venous feedback port 122.

Figure 8:
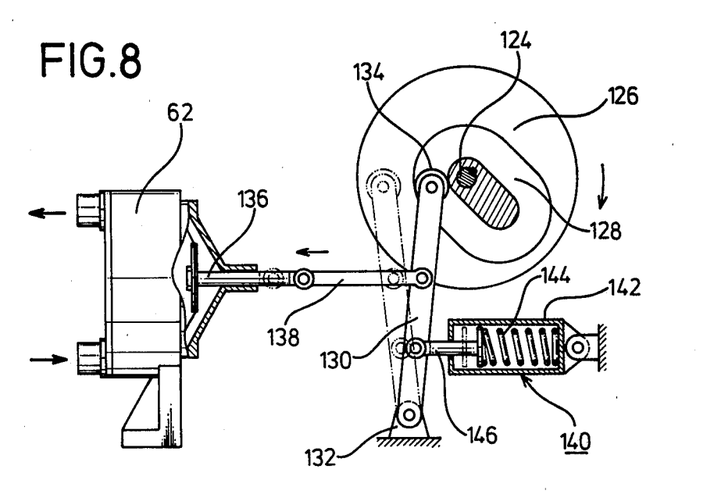
FIG. 8 is a longitudinally sectioned view of a pulsating mechanism of a further embodiment having a torque reduction means.

In FIG. 8, the driving mechanism for converting the rotary motion into the reciprocating motion includes a rotary driving shaft 124 to which a disc 126 having an eccentric channel 128 is journaled and a rocking lever 130 pivoted at its one end to a fixing base member 132 and engaged at its opposite end with the eccentric channel 128 through a follower 134. The rocking lever 130 is further connected to a plunger 136 through a connecting rod 138.

When the disc 126 is turned, the rocking lever 130 is regularly oscillated under the function of the turning eccentric channel 128 to reciprocate the plunger 138 for compressing the pump chamber rhythmically.

The rocking lever 130 is associated with a resilient means 140 which is comprised of a sleeve 142 and a coil spring 144 accommodated in the sleeve 142. One end of the coil spring 144 is pivotably connected to the rocking lever 130 through a connecting rod 146.

During the suction stroke of the pumping operation, the coil spring 144 is compressed to accumulate energy, while in the delivery stroke the accummulated energy is released abruptly through the rocking lever 130 to energize the reciprocating motion of the plunger 136. Accordingly, during each cycle of the pump operation including the suction and delivery strokes the driving torque of the pump is uniform and the driving torque at the delivery stroke is remarkably reduced.

Figure 9:
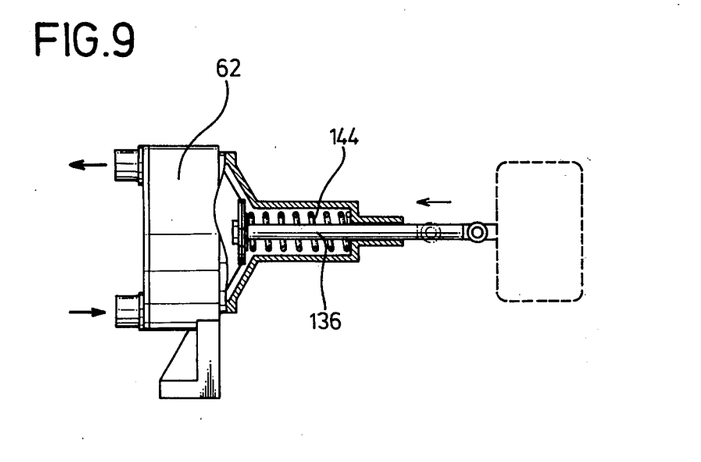
FIG. 9 is a sectional view of a torque reduction means of another embodiment.

In the embodiment shown in FIG. 9, the torque reduction spring member 144 is arranged to encircle the plunger 136 for the same purpose as the embodiment of FIG. 8.

As indicated pulsatile blood pump is driven by a cam mechanism. Many types of cams which generate a corresponding wave pattern may be produced to accord with doctor's instructions.

The accompanied Figures show a cam such as that shown in FIG. 3, wave patterns produced thereby and results of hemolytic tests.

Figure 11:
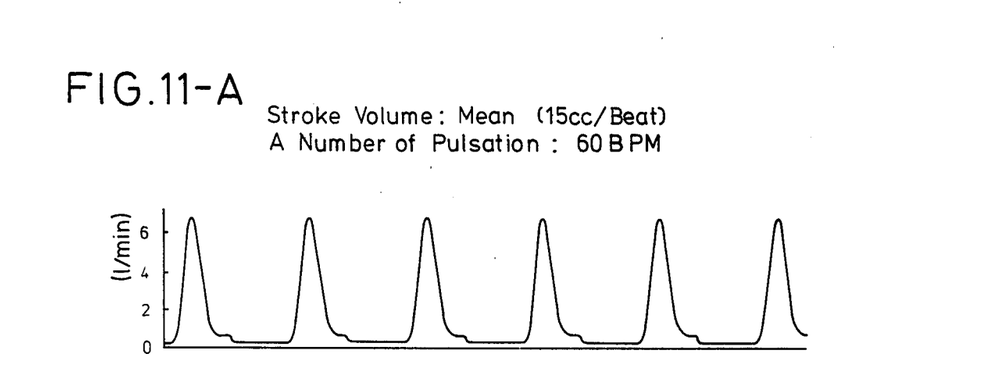
Figures 1, 11:
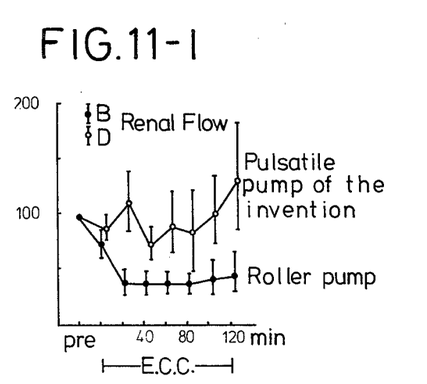

FIGS. 11a to 11c show delivery wave patters which are generated by use of the cam shown in FIG. 11h and they resemble a wave pattern for a living heart. A cam may be produced in the following manner. An electromagnetic flow meter is arranged at a delivery part of a living heart so as to record a delivery wave pattern, which in turn is integrated for drawing a basic profile of a cam, as shown in FIG. 11h.

FIGS. 11d and 11e show wave patterns of the arterial blood pressure by use of a pulsatile blood pump with the cam of FIG. 11h for animal experiment (FIG. 11d) and for clinical example (FIG. 11e), respectively. The wave patterns of arterial blood pressure show a systolic pressure of higher than 100 mmHg and a pulsatile pressure of 30 to 60 mmHg, resulting in an efficient pulsatile pump.

FIGS. 11f and 11g show results of the hemolytic tests by use of the pulsatile blood pump of the invention and a roller pump. The former shows the result of a test in vitro while the latter shows that of a clinical example. It will be apparent from the results that a degree of hemolysis is much less in the pulsatile blood pump than in the roller pump.

It will be appreciated that the pulsatile blood pump with the cam of the invention generates a wave pattern corresponding to a physiologic arterial pressure pattern and causes much less hemolysis, so that circulation of blood through peripheral vessels and function of kidney are maintained in more excellent state and a stable circulation outside the body may be achieved.

FIGS. 11c and 11j show the results of renal flow test and vascular resistance test, respectively.

The tests were made by use of a non-pulsatile roller pump and a pulsatile block pump of the invention, respectively.

As observed from FIG. 11i, the renal flow rate (ml/kg/hr) was decreased to 40% for the roller pump, whereas the rate could be maintained at 70% level or more for the pulsatile blood pump of the invention.

As observed from FIG. 11j, the renal vascular resistance (mmHg/ml) was maintained at the same level for the inventive pump, whereas the resistance was increased significantly, namely about two fold higher than the normal resistance for the roller pump.

What is claimed is:

1. A pulsatile blood pump comprising a hermetically sealed housing, a disposable, substantially enclosed sac of anticoagulative material mounted in said housing, at least one portion of said sac being formed of highly flexible material, said sac being provided with a suction port having an inlet check valve and a delivery port having an outlet check valve to constitute a closed pump unit, said suction and delivery ports extending outwardly of said housing, a pressure transmissive fluid means located within said housing surrounding at least in part said highly flexible wall of said sac and drive means for generating a pulsatile pressure in said transmissive fluid to flex said highly flexible wall producing a pumping action in said sac having a delivery stroke and a suction stroke, said drive means comprising a cam mechanism including a disc rotatable about a central axis by said drive means and provided with an eccentric channel means for rotating said disc about a central axis, and means for converting the rotary motion of said disc into reciprocating motion comprising a follower member, a stroke control means connected to said follower member, a connecting rod and a piston communicating with said transmissive fluid, and torque reduction means adapted to render said suction and delivery stroke uniform, said torque reduction means including a rocking lever on which said follower member is mounted pivoted at one end to a fixed base member and engaging at its opposite end the eccentric channel and a resilient plunger fixedly secured within a cylinder having a connecting rod attached to said rocking lever.

2. A pulsatile blood pump as claimed in claim 1, wherein the cam piece is replaceable and has a different shape to produce a different motion conformable to the physiological pulse intrinsic to a different patient.

3. A pulsatile blood pump as claimed in claim 1, wherein said resilient member comprises a fixed sleeve and a coil spring received in said sleeve member concentrically arranged about said piston.

4. A pulsatile blood pump as claimed in any of claims 2, 1, or 3, wherein the power bladder comprises a U-shaped elongated tube and the suction and delivery ports thereof are flanged connectors detachably secured to one wall of the housing.

* * * * *